(12) United States Patent
Caliskan

(10) Patent No.: US 12,392,737 B2
(45) Date of Patent: Aug. 19, 2025

(54) METHOD AND APPARATUS FOR CYCLIC IMAGING A ROCK SAMPLE

(71) Applicant: SAUDI ARABIAN OIL COMPANY, Dhahran (SA)

(72) Inventor: Sinan Caliskan, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 230 days.

(21) Appl. No.: 18/192,838

(22) Filed: Mar. 30, 2023

(65) Prior Publication Data

US 2024/0328966 A1  Oct. 3, 2024

(51) Int. Cl.
*G01N 23/046* (2018.01)
*G01N 23/083* (2018.01)
*G01N 33/24* (2006.01)

(52) U.S. Cl.
CPC ......... *G01N 23/046* (2013.01); *G01N 23/083* (2013.01); *G01N 33/24* (2013.01); *G01N 2223/3306* (2013.01)

(58) Field of Classification Search
CPC ............... G01N 23/083; G01N 23/046; G01N 23/20025; G01N 33/24; G01N 2223/3306; G01N 2223/3308; G01N 2223/6126; G01N 15/0806; G01N 15/082; G01N 15/0826; G01N 2223/616; G01N 2223/04; G01N 2015/0846; G01N 2223/419; G01N 33/241; G01N 24/081; G01N 13/02; G01N 2013/0208; G01N 2013/0241;
(Continued)

(56) References Cited

U.S. PATENT DOCUMENTS 4,799,382 A * 1/1989 Sprunt ................. G01N 15/088
73/152.05
5,036,193 A * 7/1991 Davis, Jr. ............. G01N 15/088
378/4
(Continued)

FOREIGN PATENT DOCUMENTS

WO  2012/164091 A1  12/2012
WO  2021/041325 A1  3/2021

OTHER PUBLICATIONS

Soldal, M. et al., "Rock visualization using micro-CT scanner and X-ray transparent triaxial apparatus"; Proceedings of the International Symposium of the Society of Core Analysts; SCA2017-073; pp. 1-9; Aug. 27-Sep. 1, 2017 (9 pages).
(Continued)

*Primary Examiner* — Irakli Kiknadze
(74) *Attorney, Agent, or Firm* — Osha Bergman Watanabe & Burton LLP

(57) ABSTRACT

A rock sample holder, an x-ray system, and methods are disclosed. The rock sample holder may include a body having a cavity extending from a first end of the body to a first position along a longitudinal axis. The first end of the body is open. The body comprises a radiolucent material. A
(Continued)

slit is formed through a side wall portion of the body such that the slit extends from the first end to a second position on the side wall portion between the first end and the second end. The rock sample holder may further include a base attached to a second end of the body and a cushion disposed within the cavity proximate to the first position. The body and the cushion form a rock sample chamber within the cavity.

20 Claims, 7 Drawing Sheets

(58) Field of Classification Search
CPC ........ G01N 15/088; G01N 15/08; G01N 3/08; G01N 1/28; G01N 2203/0641; G01N 2203/0242; G01N 2203/0019; G01N 2203/0048; G01N 2203/0075; G01N 2203/0298; G01N 23/223; G01N 23/20; G01N 23/2206; G01N 2223/076; G01N 2223/056; G01N 2223/045; G01N 2223/3307; G01N 2223/1016; A61B 6/4452; A61B 6/4411; A61B 6/035; A61B 6/5229; A61B 6/508; A61B 6/032; A61B 6/52; A61B 6/027; A61B 6/5258; A61B 6/4085; A61B 6/5205; G01R 33/305; G01B 11/26; E21B 49/02; G06F 30/28; G06T 17/05; G06T 11/008; G06T 7/155; G06T 7/13; G06T 2207/20036; G06T 2211/461; G06T 2207/10121; G06T 2207/20212; G06T 2207/20021; G06T 7/0004; G06T 2207/30181; G06T 2207/10081; Y02A 90/30; G06V 20/70; G06V 10/764; G01V 5/226

USPC .......... 378/4, 15, 20, 46, 50, 54, 57, 62, 68, 378/208, 19

See application file for complete search history.

(56) References Cited

U.S. PATENT DOCUMENTS

| | | | | |
|---|---|---|---|---|
| 5,109,398 | A * | 4/1992 | Hunt | G01N 15/082 378/207 |
| 5,164,590 | A * | 11/1992 | Coles | G01V 5/00 250/269.1 |
| 5,297,420 | A * | 3/1994 | Gilliland | G01N 33/241 73/38 |
| 8,068,579 | B1 * | 11/2011 | Yun | G01N 23/046 378/4 |
| 8,855,264 | B2 * | 10/2014 | Derzhi | G01N 23/087 378/54 |
| 10,247,682 | B2 * | 4/2019 | Schlecht | A61B 6/032 |
| 11,366,073 | B2 * | 6/2022 | Hansson | G01N 9/02 |
| 11,645,792 | B2 * | 5/2023 | Andrew | G06T 11/008 382/132 |
| 2016/0077023 | A1 * | 3/2016 | Alshehri | G01N 23/046 378/208 |
| 2022/0082517 | A1 * | 3/2022 | Song | G01R 33/305 |

OTHER PUBLICATIONS

Kulynycz, Vitalij et al., "The application of X-Ray Computed Microtomography for estimation of petrophysical parameters of reservoir rocks"; World Scientific News; vol. 76; pp. 91-107; 2017 (17 pages).

* cited by examiner

METHOD AND APPARATUS FOR CYCLIC IMAGING A ROCK SAMPLE

BACKGROUND

Cyclical imaging of a rock sample may be useful to compare images of the rock sample before and after the rock sample is altered or treated. Alteration of the rock sample may include chemical or mechanical alterations, among others, that may affect the physical properties of the rock sample. To adequately compare images of the rock sample, it may be necessary to house and remove the rock sample in a manner that does not damage the rock sample during imaging and allow for the rock sample to be placed in the same position at different times.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a rock sample holder. The rock sample holder includes a body having a cavity extending from a first end of the body to a first position along a longitudinal axis. The cavity may be cylindrical in shape. The first end of the body is open. The body comprises a radiolucent material. A slit is formed through a side wall portion of the body such that the slit extends from the first end to a second position on the side wall portion between the first end and the second end. The rock sample holder further includes a base attached to a second end of the body and a cushion disposed within the cavity proximate to the first position. The body and the cushion form a rock sample chamber within the cavity.

In general, in one aspect, embodiments relate to an x-ray system. The x-ray system includes a rock sample holder. The rock sample holder includes a body having a cavity extending from a first end of the body to a first position along a longitudinal axis. The first end of the body is open. The body comprises a radiolucent material. A slit is formed through a side wall portion of the body such that the slit extends from the first end to a second position on the side wall portion between the first end and the second end. The rock sample holder further includes a base attached to a second end of the body and a cushion disposed within the cavity proximate to the first position. The body and the cushion form a rock sample chamber within the cavity. The x-ray system further includes an x-ray device. The x-ray device includes an x-ray emitter, an x-ray detector, and a platform. The x-ray emitter is configured to emit x-rays towards the rock sample holder placed on the platform. The x-ray detector is configured to detect a portion of the x-rays.

In general, in one aspect, embodiments relate to a method. The method includes disposing a rock sample within a rock sample chamber of a rock sample holder and emitting, using the x-ray device, x-rays towards the rock sample disposed within the rock sample holder. The method further includes detecting, using the x-ray device, a portion of the x-rays and generating an image of the rock sample using, at least in part, the portion of the x-rays. The method further still includes removing the rock sample from the rock sample chamber of the rock sample holder by, at least in part, deforming a body of the rock sample holder using a slit formed through a side wall portion of the body.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1A:
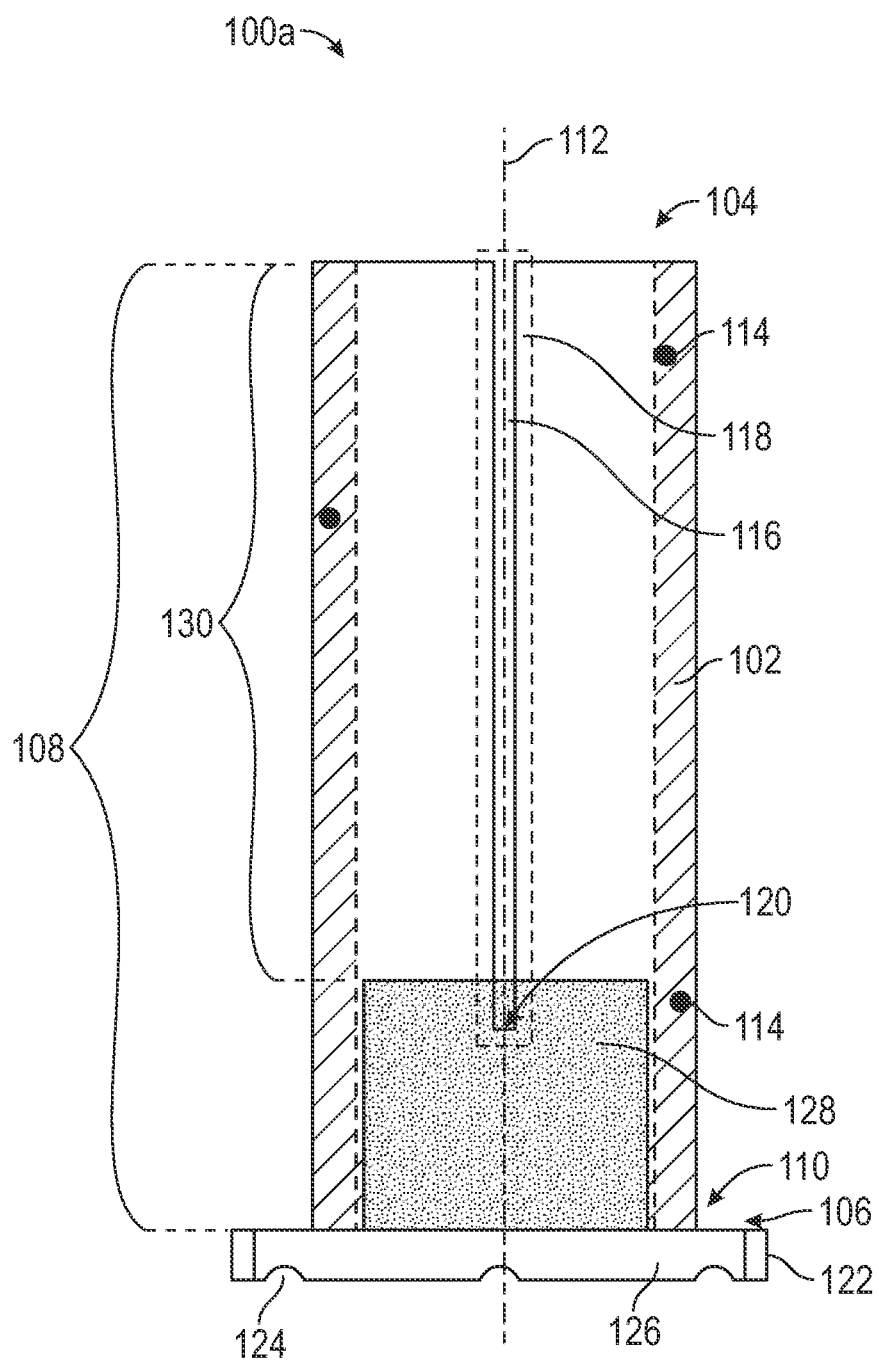
FIG. 1A illustrates a side view of a rock sample holder in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "body" includes reference to one or more of such bodies.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowchart may be omitted, repeated, and/or performed in a different order than the order shown. Accordingly, the scope disclosed herein should not be considered limited to the specific arrangement of steps shown in the flowchart.

Although multiple dependent claims are not introduced, it would be apparent to one of ordinary skill that the subject matter of the dependent claims of one or more embodiments may be combined with other dependent claims.

In the following description of FIGS. 1-5, any component described regarding a figure, in various embodiments disclosed herein, may be equivalent to one or more like-named components described regarding any other figure. For brevity, descriptions of these components will not be repeated regarding each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described regarding a corresponding like-named component in any other figure.

Methods and an apparatus are disclosed. The apparatus is a rock sample holder. A rock sample may be disposed within the rock sample holder such that the rock sample remains undamaged and stationary relative to the rock sample holder during imaging. Further, the rock sample may be disposed within the rock sample holder such that repeated images of the rock sample are comparable. Further still, the apparatus may be adaptable to hold a variety of rock sample sizes. The methods may include repeatably imaging a rock sample before and after the rock sample is altered or treated to determine a differential image.

Figure 1B:
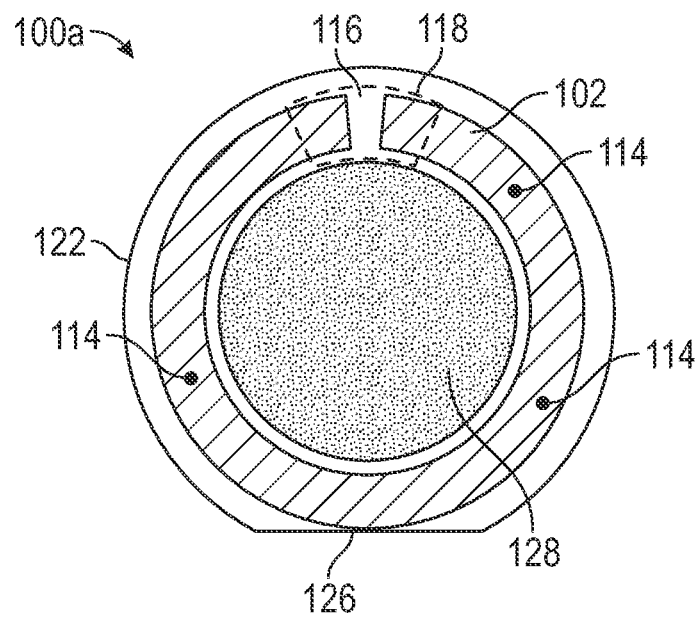
FIG. 1B illustrates a top-down view of a rock sample holder in accordance with one or more embodiments.
Figure 1C:
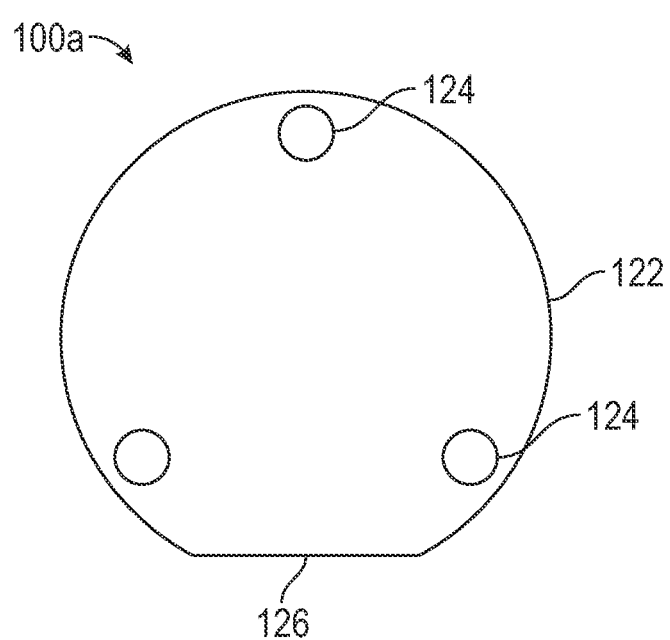
FIG. 1C illustrates a bottom-up view of a rock sample holder in accordance with one or more embodiments.

FIGS. 1A through 1C show various views of a rock sample holder (100a) in accordance with one or more embodiments. Specifically, FIG. 1A shows a side view of the rock sample holder (100a). FIG. 1B shows a top-down view of the rock sample holder (100a). FIG. 1C shows a bottom-up view of the rock sample holder (100a).

The rock sample holder (100a) includes a body (102). The body (102) includes a first end (104) and a second end (106). Further, the body (102) has a cavity (108). The cavity (108) extends from the first end (104) of the body (102) to a first position (110) along a longitudinal axis (112). The first end (104) of the body (102) is open as FIG. 1A shows. The second end (106) of the body (102) may be open or closed. In embodiments where the second end (106) of the body (102) is closed, the first position (110) may be proximate to the second end (106) of the body (102). In embodiments where the second end (106) of the body (102) is open, the first position (110) may be the second end (106) of the body (102) as FIG. 1A shows.

In some embodiments, the body (102) may be a cylinder as FIGS. 1A through 1C show. In other embodiments, the body (102) may be a cuboid. In some embodiments, the cavity (108) may be a cylinder as FIGS. 1A through 1C show. In other embodiments, the cavity (108) may be a cuboid. However, a person of ordinary skill in the art will appreciate that the body (102) and/or the cavity (108) may take still other shapes and that the body (102) and the cavity (108) need not take the same shape.

The body (102) is made, at least in part, of a radiolucent material. In the context of this disclosure, "radiolucent" means totally radiolucent or moderately radiolucent. Radiolucent materials may include, but are not limited to, carbon fiber, thermosets, thermoplastics, such as plexiglass and polycarbonates, or any composite thereof. Further, the radiolucent material may be a semi-rigid material such that the body (102) may minimally flex.

In some embodiments, the body (102) may include fiducial markers (114). The fiducial markers (114) may be spherical and made of a radiopaque material. In the context of this disclosure, "radiopaque" means totally radiopaque or moderately radiopaque. In some embodiments, the body (102) may include three or more fiducial markers (114) such that a three-dimensional coordinate system of the rock sample holder (100a) may be defined using the fiducial markers (114).

Next, a slit (116) is formed through a side wall portion (118) of the body (102). The slit (116) extends from the first end (104) of the body (102) to a second position (120) on the side wall portion (118) of the body (102). In some embodiments, the second position (120) may be between the first end (104) of the body (102) and the second end (106) of the body (102) as FIG. 1A shows. In other embodiments, the second position (120) may be the second end (106) of the body (102) and/or the first position (110).

In some embodiments, the slit (116) may extend linearly along the longitudinal axis (112) as FIG. 1A shows. In other embodiments, the slit (116) may extend non-linearly, such as helically, from the first end (104) of the body (102) to the second position (120). However, a person of ordinary skill in the art will appreciate that the slit (116) may take any path along the body (102) without departing from the scope of the disclosure.

The rock sample holder (100a) also includes a base (122). The base (122) is attached to the second end (106) of the body (102) as FIG. 1A shows. The base (122) may be attached to the second end (106) of the body (102) using adhesive, screws, bolts, nails, or any other means familiar to a person of ordinary skill in the art. In some embodiments, the body (102) may be removably fixed to the base (122) such that the body (102) may be removed from the base (122) and a different body attached to the base (122) or vice versa.

In some embodiments, the base (122) may include a connection configured to removably attach the base (122) to a platform. In some embodiments, the connection may be hemisphere cutouts (124), as FIGS. 1A and 1C show, configured to align with hemisphere extrusions of the platform. However, any means known to a person of ordinary skill in the art may be used to removably attach the base (122) to a platform.

In some embodiments, the base (122) may include a chord cutout (126) configured to aid a user in attaching the base (122) to the platform at a unique orientation, as FIGS. 1A through 1C show. However, any means known to a person of ordinary skill in the art may be used to orient the base (122) relative to the platform.

The rock sample holder (100a) also includes a cushion (128). The cushion (128) is disposed within the cavity (108) proximate to the first position (110) as FIG. 1A shows. The cushion (128) may be disposed within and removed from the cavity (108) through the first end (104) of the body (102) such that a different cushion may be alternatively disposed within the cavity (108). Lastly, the cushion (128) may be made of a vibration-damping foam or other material that will not damage a rock sample disposed within the cavity (108) of the rock sample holder (100a).

The body (102) and the cushion (128) of the rock sample holder (100a) form a rock sample chamber (130) within the cavity (108) as shown in FIG. 1A. A rock sample may ultimately be disposed within the rock sample chamber (130).

Figure 2A:
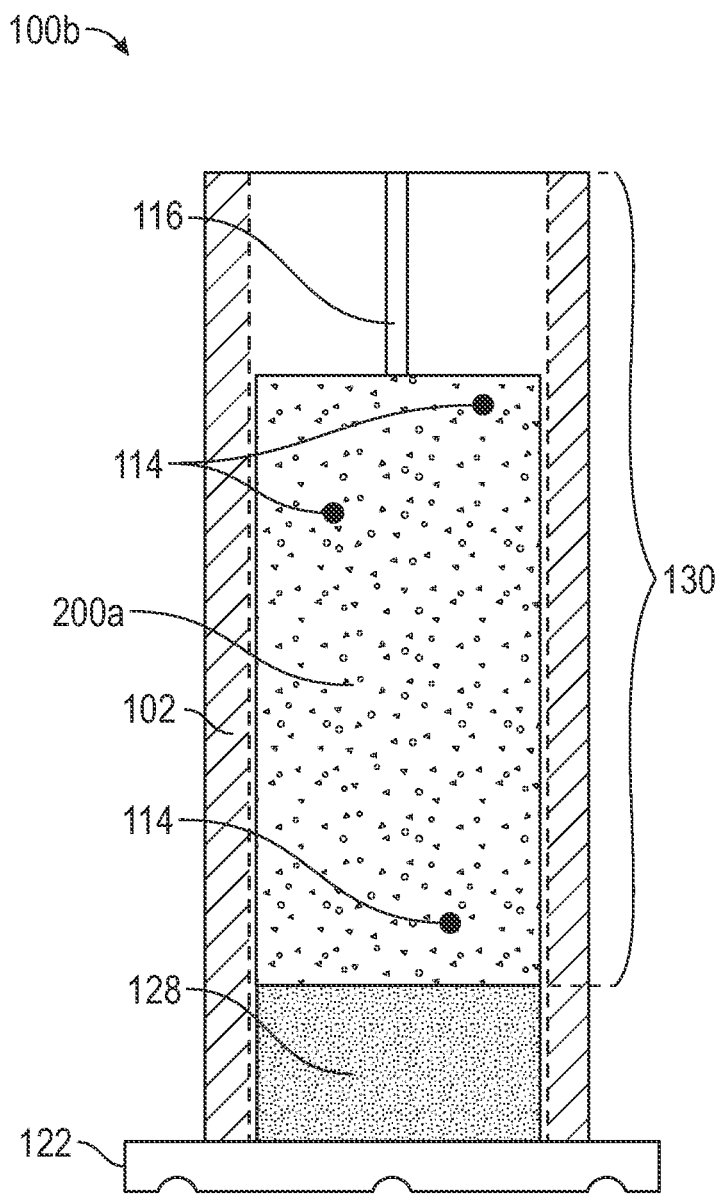
FIGS. 2A and 2B illustrate side views of a rock sample disposed within a rock sample holder in accordance with one or more embodiments.
Figure 2B:
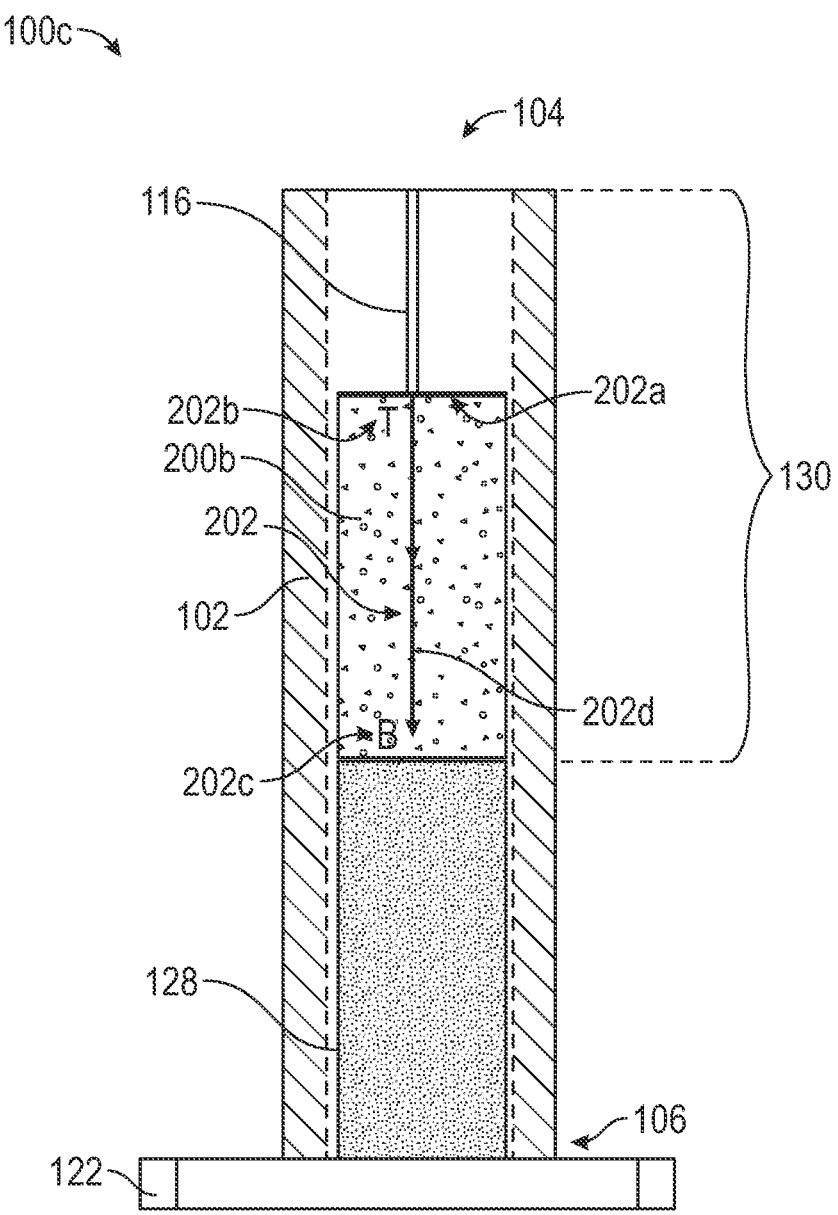

FIGS. 2A and 2B show a rock sample (200a, b) disposed within a rock sample holder (100b, c) in accordance with one or more embodiments. Specifically, FIG. 2A shows a rock sample (200a) disposed within the rock sample chamber (130) formed by the body (102) and the cushion (128) of the rock sample holder (100b). FIG. 2A may show a rock sample holder (100b) similar to the rock sample holder (100a) shown in FIGS. 1A through 1C. However, FIG. 2A now shows the fiducial markers (114) disposed within the rock sample (200a). In some embodiments, three or more fiducial markers (114) may be disposed within the rock sample (200a) such that a three-dimensional coordinate system of the rock sample (200a) may be defined using the fiducial markers (114). The rock sample chamber (130) shown in FIG. 2A may accommodate tall, wide rock samples (200a).

FIG. 2B also shows a rock sample (200b) disposed within the rock sample chamber (130) in accordance with one or more embodiments. FIG. 2B may show a rock sample holder (100c) similar to the rock sample holder (100a) shown in FIG. 1A though with a taller cushion (128). Further, FIG. 2B shows a marking (202) on the rock sample (200b). In some embodiments, the marking (202) may indicate a top surface (202a), top surface location (202b) (that may be indicated by a marking, such as "A" as shown), bottom surface location (202c) (that may be indicated by a marking, such as "B" as shown), and/or alignment indicator/directionality (202d) on the rock sample (200b). The marking (202) may be used to orient the rock sample (200b) within the rock sample chamber (130). For example, as shown in FIG. 2B, the rock sample (200b) may be oriented within the rock sample chamber (130) such that the top surface (202a) and top surface location (202b) of the marking (202) are directed towards the first end (104) of the body (102), the bottom surface location (202c) of the marking (202) is directed towards the second end (106) of the body (102), and the alignment indicator/directionality (202d) aligns with the slit (116) of the body (102). However, a person of ordinary skill in the art will appreciate that any other marking or method, which may or may not include a marking (202), may be used to denote orientation of the rock sample (200b) within the rock sample chamber (130). The rock sample chamber (130) shown in FIG. 2B may accommodate short, thin rock samples (200b).

While FIGS. 1A through 2B show only a small number of rock sample holders (100a-c), a person of ordinary skill in the art will appreciate that the rock sample holder (100a-c) may be configured and/or modified to accommodate a range of rock samples (200a, b) of various heights, widths, and shapes.

Figure 3:
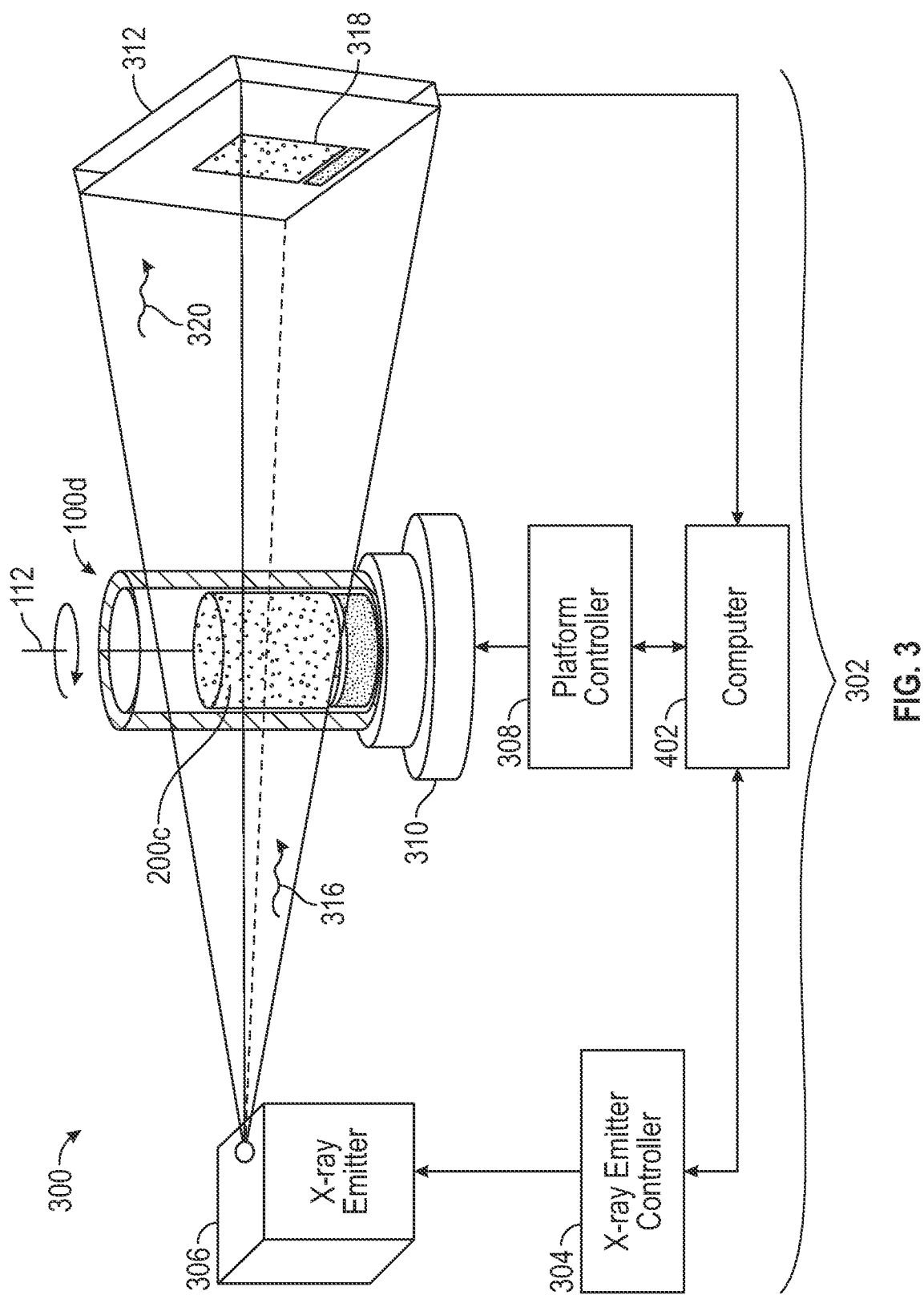
FIG. 3 illustrates an x-ray system in accordance with one or more embodiments.

Turning to FIG. 3, FIG. 3 illustrates an x-ray system (300) in accordance with one or more embodiments. The x-ray system (300) includes an x-ray device (302), a rock sample holder (100d), and a rock sample (200c). In some embodiments, the x-ray device (302) may include a computer (402), an x-ray emitter controller (304), an x-ray emitter (306), a platform controller (308), a platform (310), and an x-ray detector (312), among other components.

In some embodiments, the rock sample holder (100d) may be placed on the platform (310) of the x-ray device (302). In the context of this disclosure, "placed" may refer to the rock sample holder (100d) resting on the platform (310), the rock sample holder (100d) being fixed to the platform (310), or the rock sample holder (100d) being removably fixed to the platform (310). In some embodiments, the platform (310) may remain stationary. In other embodiments, the platform (310) may rotate around the longitudinal axis (112). In these embodiments, a platform controller (308) may control or trigger when, at what rate, and for how long the platform (310) rotates.

The x-ray emitter (306) of the x-ray device (302) may emit x-rays (316) using an x-ray tube (not shown). The x-ray tube may generate electromagnetic radiation in the form of x-rays (316) by accelerating high-voltage electrons released at a cathode of the x-ray tube to collide with a metal anode. In some embodiments, the x-ray emitter (306) may include an x-ray filter such that only hard x-rays (316) with photon energies above approximately 150 kiloelectron volts (keV) exit the x-ray emitter (306). This process is commonly referred to as "beam hardening." In some embodiments, the x-ray emitter (306) may also include a collimator to focus the x-rays (316). The x-ray filter and/or collimator may alternatively exist external to the x-ray emitter (306).

The x-ray emitter controller (304) may control or trigger when, at what rate, at what energy, how many, and for how long x-rays (316) are emitted from the x-ray emitter (306). For example, the number of x-rays (316) generated by the x-ray emitter (306) may be controlled by varying the milliamperage (mA) of the x-ray tube. Further, the energy of the x-rays (316) generated may be controlled by varying the kilovoltage (kV) of the x-ray tube. Further still, how long the x-rays (316) are emitted may be controlled by varying the exposure time.

In some embodiments, the x-ray emitter (306) may remain stationary as shown in FIG. 3. In other embodiments, the x-ray emitter (306) may rotate simultaneously with an x-ray detector (312) around a stationary platform (310) around the longitudinal axis (112).

In the context of this disclosure, the x-ray emitter (306) may emit x-rays (316) towards the rock sample (200c) disposed within the rock sample holder (100d) placed on the platform (310). The emitted x-rays (316) will pass through or mostly pass through radiolucent materials, such as the body (102) of the rock sample holder (100d). Some emitted x-rays (316) may travel to and be detected by the x-ray detector (312). Alternatively, some emitted x-rays (316) will be absorbed by radiopaque materials, such as the fiducial markers (114). As such, these x-rays (316) may not travel to or be detected by the x-ray detector (312).

In some embodiments, the x-ray detector (312) may be an imaging detector such as, but not limited to, an x-ray film, an image plate, or a flat panel detector. Further, some x-ray detectors (312) may be digital detectors in which the detected x-rays (320) are converted into electrical signals such that an image (318) may be displayed digitally, such as on a computer (402).

In some embodiments, the x-ray detector (312) may generate a "negative image" (318) where detected x-rays (320) appear black or gray and undetected x-rays appear white at specific locations on the x-ray detector (312). This process may be referred to as radiography and may generate a single two-dimensional projection image (318) of the rock sample (200c). In these embodiments, the x-ray device (302) may be a radiographic device. In other embodiments, such as when the platform (310) or the x-ray emitter (306) and the x-ray detector (312) rotate around the longitudinal axis (112), the x-ray detector (312) may detect various amounts of x-rays (320) at different times and different positions to generate a sinogram. An inverse Radon transform may then be applied to the sinogram, using a computer (402), to reconstruct a three-dimensional image (318) of the rock sample (200c). This process may be referred to as computed tomography (CT) or micro-computed tomography (μCT), if increased image resolution is desirable. In these embodiments, the x-ray device (302) may be a CT device or a μCT device. Hereinafter, any "image" may refer to a two-dimensional projection image (318) or a three-dimensional image (318). Lastly, note that the degree of grayscale at each specific location within an image (318) may be based, at least in part, on the density of the material through which the x-rays (316) traveled.

Figure 4:
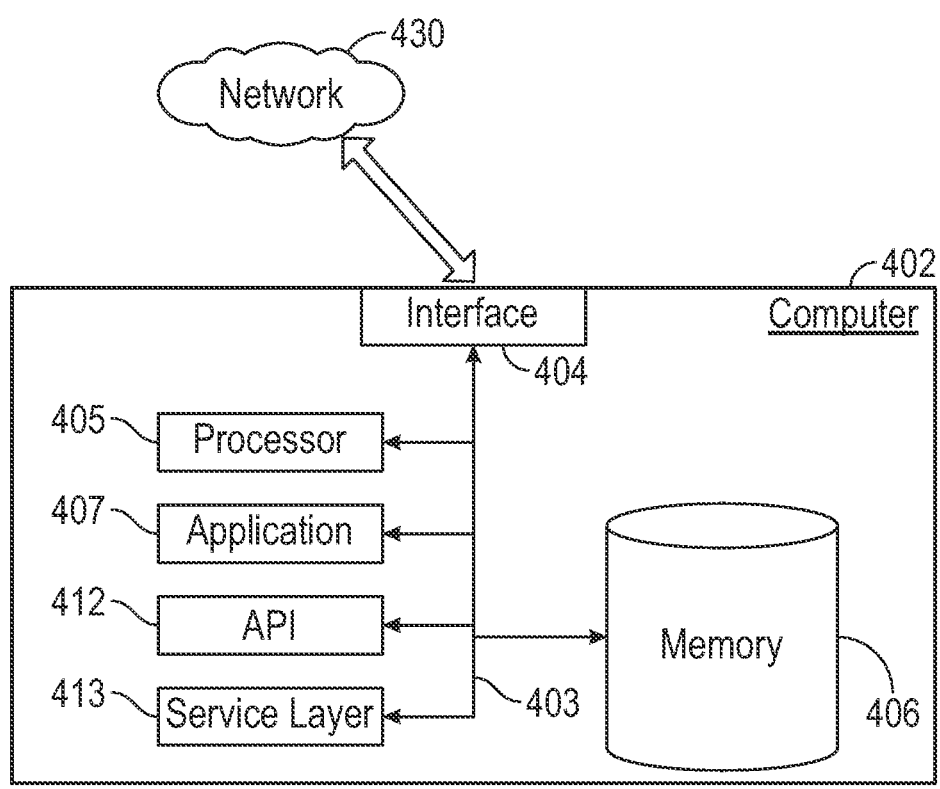
FIG. 4 illustrates a computer in accordance with one or more embodiments.

FIG. 4 illustrates a computer (402) in accordance with one or more embodiments. In some embodiments, the computer (402) may be a part of the x-ray device (302) as described in FIG. 3. In these embodiments, the computer (402) may be communicably coupled to the x-ray emitter controller (304), the platform controller (308), and/or the x-ray detector (312) via a network (430). In other embodiments, the computer (402) may be separate from the x-ray device (302). Specifically, the computer (402) may provide instructions to the x-ray emitter controller (304) and/or the platform controller (308). Further, the computer (402) may receive information from the x-ray emitter controller (304), platform controller (308), and/or x-ray detector (312). For example, the computer (402) may receive a sinogram from the x-ray detector (312). Received information may be used, at least in part, by the computer (402) to generate a digital image (318) of the rock sample (200*c*).

In general, the computer (402) is intended to encompass any computing device. A computing device may include a server, desktop computer, laptop/notebook computer, wireless data port, smart phone, personal data assistant (PDA), tablet computing device, one or more processors (405) within these devices, or any other suitable processing device, including both physical and/or virtual instances. The computer (402) may include an input device, such as a keypad, keyboard, touch screen, or other device that can accept user information, such as mA and kV settings. Additionally, the computer (402) may include an output device that conveys information to a user, such as a digital image (318) of the rock sample (200*c*).

The computer (402) can serve in a role as a client, network component, a server, a database or other persistency, or any other component (or a combination of roles). The illustrated computer (402) may be communicably coupled with a network (430) and/or other components of the x-ray device (302). In some implementations, one or more components of the computer (402) may be configured to operate within environments, including cloud-computing-based, local, global, or other environment (or a combination of environments).

Each of the components of the computer (402) can communicate using a system bus (403). In some implementations, any or all of the components of the computer (402), both hardware or software (or a combination of hardware and software), may interface with each other or the interface (404) (or a combination of both) over the system bus (403) using an application programming interface (API) (412) or a service layer (413) (or a combination of the API (412) and service layer (413). The API (412) may include specifications for routines, data structures, and object classes. The API (412) may be either computer-language independent or dependent and refer to a complete interface, a single function, or even a set of APIs. The service layer (413) provides software services to the computer (402) or other components (whether or not illustrated) that are communicably coupled to the computer (402). The functionality of the computer (402) may be accessible for all service consumers using this service layer. Software services, such as those provided by the service layer (413), provide reusable, defined business functionalities through a defined interface. For example, the interface may be software written in JAVA, C++, or other suitable language providing data in extensible markup language (XML) format or another suitable format. While illustrated as an integrated component of the computer (402), alternative implementations may illustrate the API (412) or the service layer (413) as stand-alone components in relation to other components of the computer (402) or other components (whether or not illustrated) that are communicably coupled to the computer (402). Moreover, any or all parts of the API (412) or the service layer (413) may be implemented as child or sub-modules of another software module, enterprise application, or hardware module without departing from the scope of this disclosure.

The computer (402) includes an interface (404). Although illustrated as a single interface (404) in FIG. 4, two or more interfaces (404) may be used according to particular needs, desires, or particular implementations of the computer (402). The interface (404) is used by the computer (402) for communicating with other systems in a distributed environment that are connected to the network (430). Generally, the interface (404) includes logic encoded in software or hardware (or a combination of software and hardware) and operable to communicate with the network (430). More specifically, the interface (404) may include software supporting one or more communication protocols associated with communications such that the network (430) or interface's hardware is operable to communicate physical signals within and outside of the illustrated computer (402).

The computer (402) includes at least one computer processor (405). Although illustrated as a single computer processor (405) in FIG. 4, two or more processors may be used according to particular needs, desires, or particular implementations of the computer (402). Generally, the computer processor (405) executes instructions and manipulates data to perform the operations of the computer (402) and any algorithms, methods, functions, processes, flows, and procedures as described in the instant disclosure. The computer processor (405) may be a central processing unit (CPU) and/or a graphics processing unit (GPU).

The computer (402) also includes a memory (406) that holds data for the computer (402) or other components (or a combination of both) that can be connected to the network (430). For example, memory (406) can be a database storing imaging data detected by the x-ray detector (312) of the x-ray device (302). Although illustrated as a single memory (406) in FIG. 4, two or more memories may be used according to particular needs, desires, or particular implementations of the computer (402) and the described functionality. While memory (406) is illustrated as an integral component of the computer (402), in alternative implementations, memory (406) can be external to the computer (402).

The application (407) is an algorithmic software engine providing functionality according to particular needs, desires, or particular implementations of the computer (402), particularly with respect to functionality described in this disclosure. For example, application (407) can serve as one or more components, modules, applications, etc. Further, although illustrated as a single application (407), the application (407) may be implemented as multiple applications (407) on the computer (402). In addition, although illustrated as integral to the computer (402), in alternative implementations, the application (407) can be external to the computer (402).

There may be any number of computers (402) associated with, or external to, a computer system containing a computer (402), wherein each computer (402) communicates over network (430). Further, the term "client," "user," and other appropriate terminology may be used interchangeably as appropriate without departing from the scope of this disclosure. Moreover, this disclosure contemplates that many users may use one computer (402), or that one user may use multiple computers (402).

Figure 5:
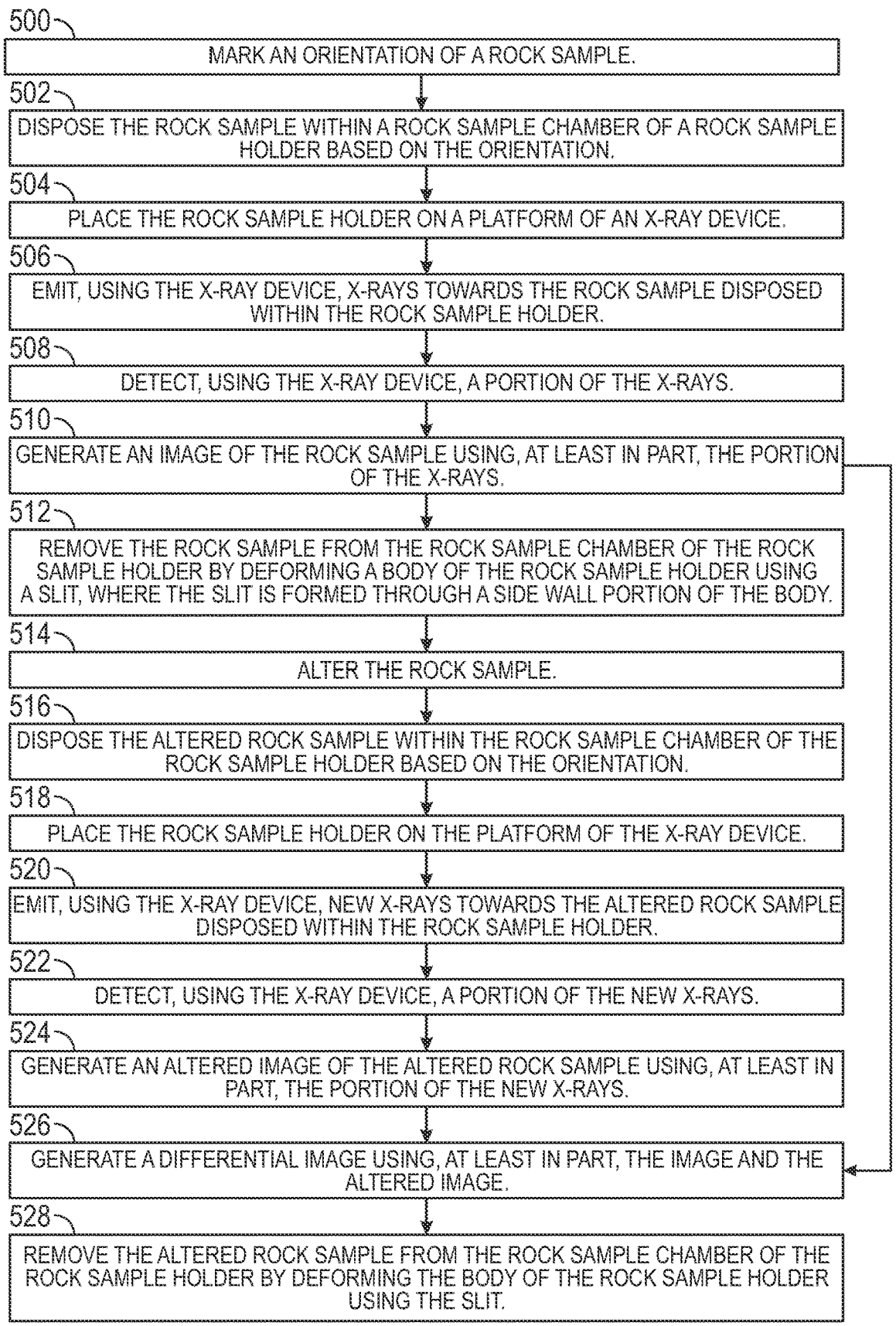
FIG. 5 shows a flowchart in accordance with one or more embodiments.

FIG. 5 shows a flowchart in accordance with one or more embodiments. The flowchart outlines a method of determining an image (318), an altered image, and a differential image of a rock sample (200c) disposed within a rock sample holder (100d).

In step 500, an orientation may be marked on a rock sample (200c). In some embodiments, the orientation may be marked on the rock sample (200c) as illustrated on or similar to the rock sample (200b) in FIG. 2B. The orientation may orient the rock sample (200c) relative to the rock sample holder (100d) along one or more degrees-of-freedom. For example, the marking (202) on the rock sample (200b) in FIG. 2B orients the rock sample (200b) relative to the rock sample holder (100c) along two degrees-of-freedom by designating the top surface location (202b) using a 'T' and the bottom surface location (202c) using a 'B' and that the alignment indicator/directionality (202d) aligns with the slit (116) of the body (102). In other embodiments, the marking (202) may be simpler or more complex than the marking (202) shown in FIG. 2B. Further, in still other embodiments, fiducial markers (114), as shown in FIG. 1A or 2A, may act as a portion of or all of the marking.

In step 502, the rock sample (200c) is disposed within a rock sample chamber (130) of a rock sample holder (100d). In some embodiments, the rock sample (200c) may be disposed within the rock sample chamber (130) of the rock sample holder (100d) based on the marked orientation.

In step 504, the rock sample holder (100d) is placed on a platform (310) of an x-ray device (302). The x-ray device (302) may be a radiographic device, a CT device, or a μCT device, as described in reference to FIG. 3. In some embodiments, hemisphere cutouts (124) on the base (122) align with hemisphere extrusions on the platform (310). In some embodiments, a chord cutout (126) on the base (122) also aligns with a chord cutout on the platform (310).

In step 506, x-rays (316) are emitted from the x-ray device (302) towards the rock sample (200c) disposed within the rock sample holder (100d). As previously described, the x-ray emitter (306) of the x-ray device (302) emits the x-rays (316). The x-rays (316) will pass through or moderately pass through radiolucent materials. The x-rays (316) will be absorbed or moderately absorbed by radiopaque materials.

In step 508, a portion of the x-rays (320) are detected by the x-ray device (302). Specifically, the portion of the x-rays (320) that pass through or moderately pass through the rock sample (200c) disposed in the rock sample holder (100d) may be detected by an x-ray detector (312) of the x-ray device (302).

In step 510, an image (318) of the rock sample (200c) is generated using, at least in part, the portion of the x-rays (320). In some embodiments, the image (318) may be a two-dimensional projection image (318) of the rock sample (200c) (i.e., a radiographic image). In other embodiments, the image (318) may be a three-dimensional image (i.e., a computed or micro-computed tomographic image) of the rock sample (200c). In these embodiments, the x-ray detector (312) may detect a sinogram that is then converted to an image (318) by applying an inverse Radon transform to the sinogram.

In step 512, the rock sample (200c) is removed from the rock sample chamber (130) of the rock sample holder (100d). To remove the rock sample (200c) without damaging the rock sample (200c), the body (102) of the rock sample holder (100d) may be deformed, at least in part, using the slit (116) formed through the side wall portion (118) of the body (102). In some embodiments, a user may apply a force to the slit (116) to deform the body (102) and, thus, dislodge the rock sample (200c) from the rock sample chamber (130) of the rock sample holder (100d) free of damage.

In step 514, the rock sample (200c) is altered. The rock sample (200c) may be mechanically and/or chemically altered. In some embodiments, alteration may affect the physical properties of the rock sample (200c), such as permeability and porosity.

In step 516, the altered rock sample is disposed within the rock sample chamber (130) of the rock sample holder (100d). In some embodiments, the altered rock sample may be disposed within the rock sample chamber (130) of the rock sample holder (100d) based on the marked orientation such that the altered rock sample is in the same or nearly the same orientation as the rock sample (200c) was relative to the rock sample holder (100d) in step 502.

In step 518, the rock sample holder (100d) that contains the altered rock sample is placed on the platform (310) of the x-ray device (302). This step may be similar to step 504.

In step 520, new x-rays are emitted from the x-ray device (302) towards the altered rock sample disposed within the rock sample holder (100d). This step may be similar to step 506.

In step 522, a portion of the new x-rays are detected by the x-ray device (302). This step may be similar to step 508.

In step 524, an altered image of the altered rock sample is generated using, at least in part, the portion of the new x-rays. In some embodiments, the altered image may be a two-dimensional projection image of the altered rock sample (i.e., a radiographic image). In other embodiments, the altered image may be a three-dimensional image (i.e., a computed or micro-computed tomographic image) of the altered rock sample. This step may be similar to step 510.

In step 526, a differential image is generated using, at least in part, the image (318) from step 510 and the altered image from step 524. In some embodiments, the differential image may be determined by aligning the manifestation of the fiducial markers (114) in the image (318) with the manifestation of the fiducial markers (114) in the altered image and subtracting one image from the other image. In other embodiments, the differential image may be determined by immediately subtracting one image from the other image if the rock sample (200c) and the altered rock sample were both aligned within the rock sample holder (100d) using the marking (202).

The differential image may be used to assess how the chemical and/or mechanical alteration of the rock sample (200c) affects physical properties, such as porosity and density, of the rock sample (200c). Such information may then be used, at least in part, to inform various plans associated with an oil field lifecycle. For example, the change in physical properties of the rock sample (200c) may be used to inform well drilling strategies, well completion strategies, and/or well stimulation strategies.

In step 528, the altered rock sample is removed from the rock sample chamber (130) of the rock sample holder (100d). To remove the altered rock sample, the body (102) of the rock sample holder (100d) may be deformed, at least in part, using the slit (116). In some embodiments, a user may apply a force to the slit (116) to deform the body (102) and, thus, dislodge the altered rock sample from the rock sample chamber (130) of the rock sample holder (100d). This step may be similar to step 512.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A rock sample holder comprising:
a body having a cavity extending from a first end of the body to a first position along a longitudinal axis, wherein the first end of the body is open;
a base attached to a second end of the body; and
a cushion disposed within the cavity proximate to the first position;
wherein the body comprises a radiolucent material;
wherein a slit is formed through a side wall portion of the body such that the slit extends from the first end to a second position on the side wall portion between the first end and the second end; and
wherein the body and the cushion form a rock sample chamber within the cavity.

2. The rock sample holder of claim 1, wherein the slit extends linearly along the longitudinal axis.

3. The rock sample holder of claim 1, wherein the slit is configured to act as an alignment indicator.

4. The rock sample holder of claim 1, wherein the first position is the second end of the body.

5. The rock sample holder of claim 1, wherein the base comprises a connection configured to removably attach the base to a platform.

6. The rock sample holder of claim 5, wherein the connection comprises hemisphere cutouts configured to align with hemisphere extrusions of the platform.

7. The rock sample holder of claim 1, wherein the cavity is cylindrical.

8. The rock sample holder of claim 1, wherein the radiolucent material comprises carbon fiber.

9. The rock sample holder of claim 1, wherein the cushion comprises a vibration-damping foam.

10. The rock sample holder of claim 1, wherein the body comprises fiducial markers.

11. The rock sample holder of claim 10, wherein the fiducial markers comprise a radiopaque material.

12. An x-ray system comprising:
a rock sample holder comprising:
a body having a cavity extending from a first end of the body to a first position along a longitudinal axis, wherein the first end of the body is open,
a base attached to a second end of the body, and
a cushion disposed within the cavity proximate to the first position,
wherein the body comprises a radiolucent material,
wherein a slit is formed through a side wall portion of the body such that the slit extends from the first end to a second position on the side wall portion between the first end and the second end, and
wherein the body and the cushion form a rock sample chamber within the cavity; and
an x-ray device comprising:
an x-ray emitter,
an x-ray detector, and
a platform,
wherein the x-ray emitter is configured to emit x-rays towards the rock sample holder placed on the platform, and
wherein the x-ray detector is configured to detect a portion of the x-rays.

13. The x-ray system of claim 12, further comprising a computer processor configured to:
trigger the x-ray emitter to emit the x-rays;
trigger the platform to rotate about the longitudinal axis;
receive a signal from the x-ray detector; and
generate an image based, at least in part, on the signal.

14. The x-ray system of claim 12, wherein the x-ray device comprises a micro-computed tomography device.

15. A method comprising:
disposing a rock sample within a rock sample chamber of a rock sample holder, the rock sample holder comprising:
a body having a cavity extending from a first end of the body to a first position along a longitudinal axis, wherein the first end of the body is open,
a base attached to a second end of the body, and
a cushion disposed within the cavity proximate to the first position,
wherein the body comprises a radiolucent material,
wherein a slit is formed through a side wall portion of the body such that the slit extends from the first end to a second position on the side wall portion between the first end and the second end, and
wherein the body and the cushion form the rock sample chamber within the cavity;
placing the rock sample holder on a platform of an x-ray device, the x-ray device comprising:
an x-ray emitter,
an x-ray detector, and
the platform;
emitting, using the x-ray device, x-rays towards the rock sample disposed within the rock sample holder;
detecting, using the x-ray device, a portion of the x-rays;
generating an image of the rock sample using, at least in part, the portion of the x-rays; and
removing the rock sample from the rock sample chamber of the rock sample holder by, at least in part, deforming the body of the rock sample holder using the slit.

16. The method of claim 15, further comprising:
altering the rock sample;
disposing the altered rock sample within the rock sample chamber of the rock sample holder;
placing the rock sample holder on the platform of the x-ray device;
emitting, using the x-ray device, new x-rays towards the altered rock sample disposed within the rock sample holder;
detecting, using the x-ray device, a portion of the new x-rays;
generating an altered image of the altered rock sample using, at least in part, the portion of the new x-rays;
generating a differential image using, at least in part, the image and the altered image; and
removing the altered rock sample from the rock sample chamber of the rock sample holder by, at least in part, deforming the body of the rock sample holder using the slit.

17. The method of claim 16, wherein disposing the altered rock sample comprises:
marking an orientation of the rock sample; and
disposing the altered rock sample within the rock sample chamber of the rock sample holder based on the orientation.

18. The method of claim 16, wherein generating the differential image comprises aligning manifestations of fiducial markers in the image with manifestations of the fiducial markers in the altered image.

19. The method of claim 15, wherein disposing the rock sample comprises:
 marking an orientation of the rock sample; and
 disposing the rock sample within the rock sample chamber of the rock sample holder based on the orientation.

20. The method of claim 15, wherein the rock sample comprises fiducial markers.

\* \* \* \* \*